US00PP27918P2

(12) United States Plant Patent
Probst

(10) Patent No.: US PP27,918 P2
(45) Date of Patent: Apr. 18, 2017

(54) ***COREOPSIS* PLANT NAMED 'RED ELF'**

(50) Latin Name: ***Coreopsis* hybrid**
Varietal Denomination: Red Elf

(71) Applicant: Darrell R. Probst, Hubbardston, MA (US)

(72) Inventor: Darrell R. Probst, Hubbardston, MA (US)

( * ) Notice: Subject to any disclaimer, the term of this patent is extended or adjusted under 35 U.S.C. 154(b) by 97 days.

(21) Appl. No.: 14/545,032

(22) Filed: Mar. 18, 2015

(51) Int. Cl.
*A01H 5/02* (2006.01)

(52) U.S. Cl.
USPC ..... Plt./417

(58) Field of Classification Search
USPC ..... Plt./417
See application file for complete search history.

(56) References Cited

PUBLICATIONS

American Nurseryman 2015 Dec. 2014, retrieved on Aug. 4, 2016, retrieved from the Internet at <http://www.amerinursery.com/content/AN/pdf/2015_AN_NewPlants.pdf> pp. 4 and 36.*
Emerald Coast Grower Starter Plants 2014-2015 catalog pp. 1-3, 8-9 and 26-27.*
Pioneer Gardens, Inc. 2014-2015 Program and Availability, retrieved on Aug. 18, 2016, retrieved from the Internet at <https://nebula.wsimg.com/a8e14aaf5f2c1ab73574f0980ec0bb03?AccessKeyId=D4DC3ED90C9EAD58C2B4&disposition=0&alloworigin=1> Aug. 27, 2014, pp. 1-20.*

* cited by examiner

*Primary Examiner* — June Hwu
(74) *Attorney, Agent, or Firm* — Penny J. Aguirre

(57) ABSTRACT

A new cultivar of hybrid *Coreopsis* named 'Red Elf' that is characterized by its compact plant habit, its nearly sterile florets result in a floriferous and long bloom season that does not require deadheading with bloom commencing in late-June and lasting until frost in Connecticut, its large inflorescences with ray florets that are deep velvety red in color, its cold hardiness at least to U.S.D.A. Zone 5a, and its resistance to powdery mildew and leaf spot.

2 Drawing Sheets

Botanical classification: *Coreopsis* hybrid.
Variety denomination: 'Red Elf'.

BACKGROUND OF THE INVENTION

The present invention relates to a new and distinct cultivar of *Coreopsis* plant, botanically of hybrid origin and known as *Coreopsis* 'Red Elf' and will be referred to hereinafter by its cultivar name, 'Red Elf'. The new cultivar of *Coreopsis* is an herbaceous perennial grown for landscape and container use.

The new invention arose from an ongoing controlled breeding program in Hubbardston, Mass. The objective of the breeding program is to develop hybrid cultivars of *Coreopsis* with unique and superior garden attributes. In particular, to develop long-lived cultivars in a wide range of flower colors and plant forms that have sturdy plant habits, exhibit a true perennial habit, and are cold hardy to at least U.S.D.A Zone 5a.

The new cultivar arose from a cross made by the Inventor in August of 2010 in his test garden in Hubbardston, Mass. between an unnamed, proprietary plant in the Inventor's breeding program, reference no. Q1 09-10 (not patented), as the female parent and pollen that was pooled from a variety of unnamed, proprietary plants (not patented) from his breeding program as the male parent (all nearly sterile). The exact male parentage is therefore unknown. 'Red Elf' was selected in September 2011 as a single unique plant amongst the resulting seedlings.

Asexual reproduction of the new cultivar was first accomplished by stem cuttings under the direction of the Inventor in Kensington, Conn. in September of 2011. Asexual propagation by stem cuttings has determined that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'Red Elf' as a new and distinct cultivar of *Coreopsis*.

1. 'Red Elf' exhibits a compact plant habit reaching an average of 30 cm in height and 38 cm in width.
2. 'Red Elf' is nearly sterile and exhibits a floriferous and long bloom season that does not require deadheading, commencing bloom in late June and blooming until frost in Kensington, Conn.
3. 'Red Elf' exhibits large inflorescences with ray florets that are deep velvety red in color.
4. 'Red Elf' exhibits cold hardiness at least to U.S.D.A. Zone 5a.
5. 'Red Elf' exhibits resistance to powdery mildew and leaf spot.

The female parent differs from 'Red Elf' in having inflorescences with ray florets that are white in color and blushed with pink, especially in cooler temperatures. 'Red Elf' can be most closely compared to the *Coreopsis* cultivars 'Mercury Rising' (U.S. Plant Pat. No. 24,689) and 'Center Stage' (U.S. Plant Pat. No. 22,707). 'Mercury Rising' is similar to 'Red Elf' in being resistant to powdery mildew and leaf spot, in having large inflorescences with ray florets that are red in color, and in having a long bloom season that does not require deadheading. 'Mercury Rising' differs from 'Red Elf' in having a more openly branched and wide spreading plant habit. 'Center Stage' is similar to 'Red Elf' in having red ray florets. 'Center Stage' differs from 'Red Elf' in having flowers that are pink-red in color, in having ray florets that are narrower and more widely spaced apart (making the inflorescence less full in appearance), in having a taller plant height and a more open, less compact plant habit.

BRIEF DESCRIPTION OF THE DRAWINGS

The accompanying colored photographs illustrate the overall appearance and distinct characteristics of the new *Coreopsis*. The photographs were taken of a three month-old plant (from a 128-cell plug) of 'Red Elf' as grown in outdoors in a one-gallon container in Cheshire, Conn.

The photograph in FIG. 1 provides a view of 'Red Elf' in bloom.

Figure 1:
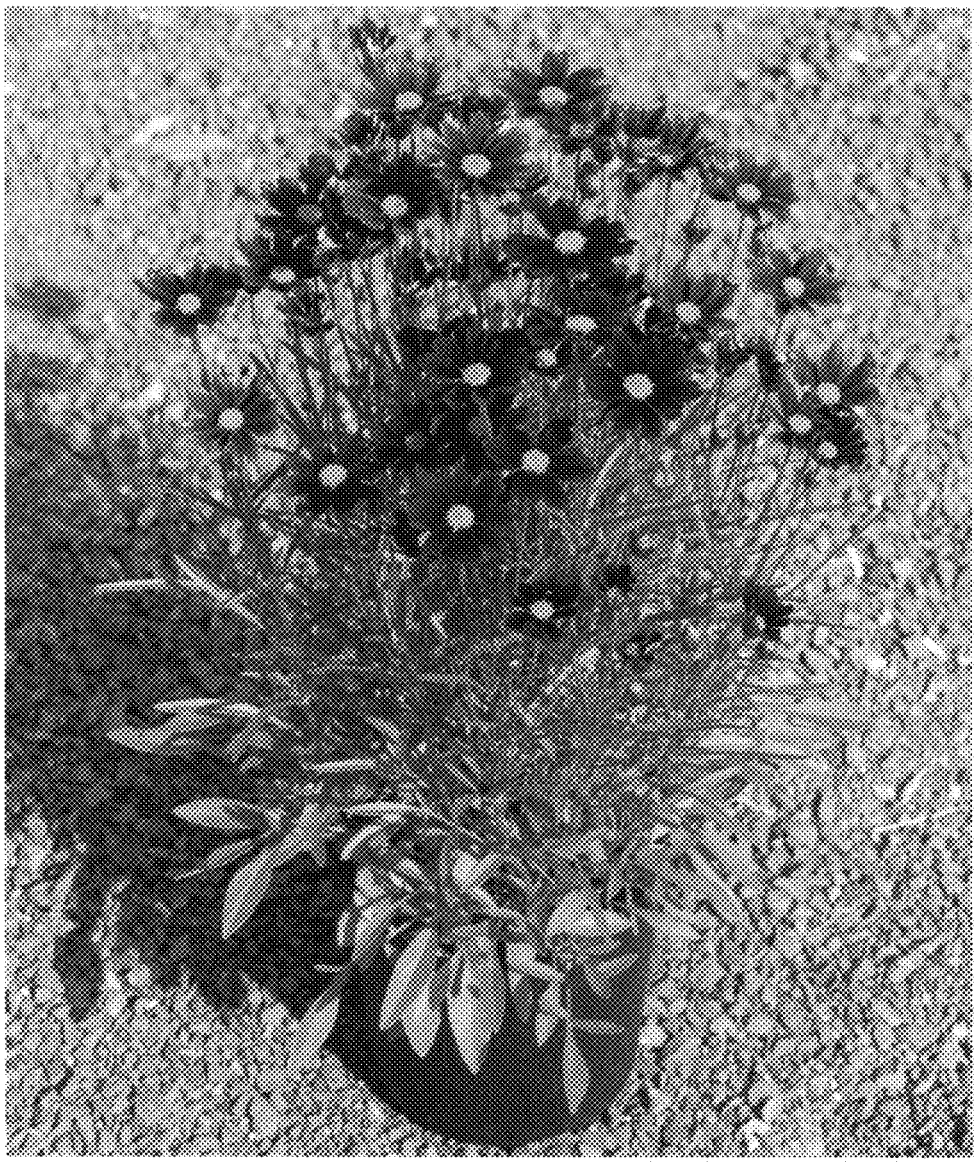
Figure 2:
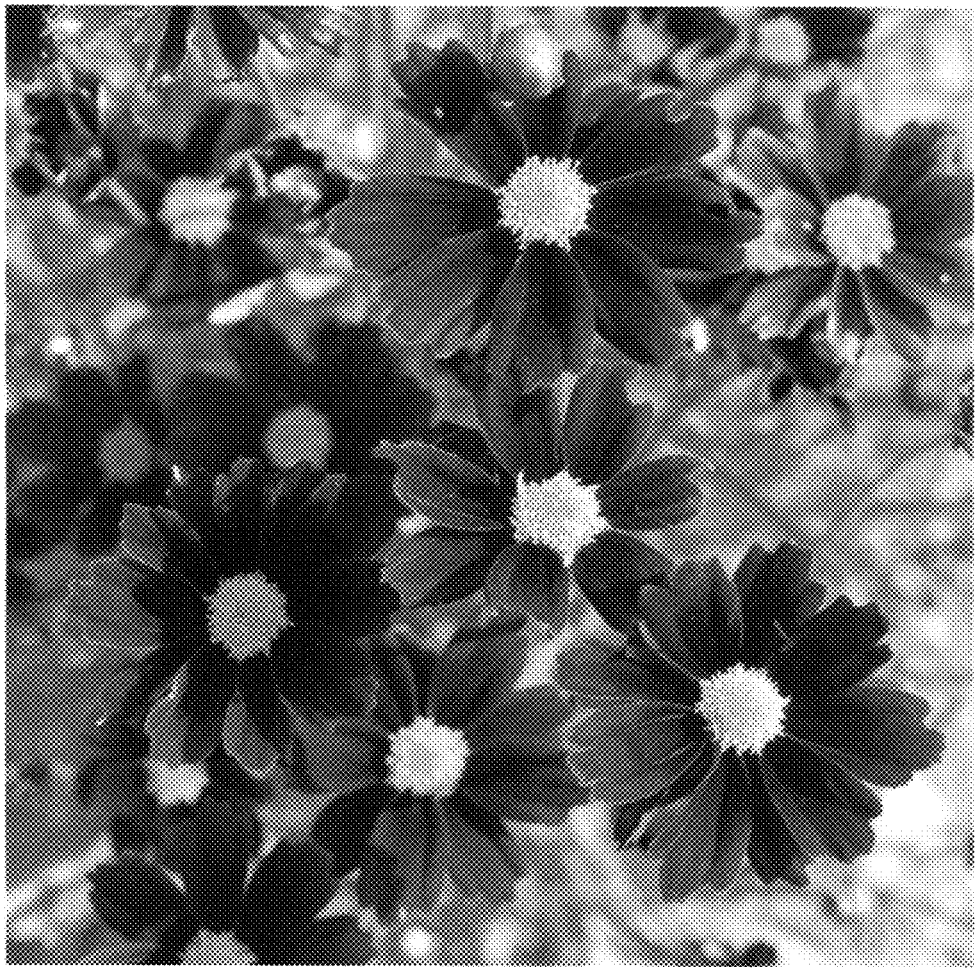

The photograph in FIG. 2 provides a close-up view of the inflorescences, showing their fully opened color, of 'Red Elf'.

The colors in the photographs are as close as possible with the digital photography techniques available, the color values cited in the detailed botanical description accurately describe the colors of the new *Coreopsis*.

DETAILED BOTANICAL DESCRIPTION

The following is a detailed description of plants of the new cultivar three months in age as grown outdoors in one-gallon containers in Kensington, Conn. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Blooms from late-June until frost in Kensington, Conn.

*Plant type*.—Herbaceous perennial.

*Plant habit*.—Compact and densely branched with upright flowers borne above the stems.

*Height and spread*.—An average of 30 cm in height and 38 cm in width.

*Cold hardiness*.—At least in U.S.D.A Zone 5a.

*Diseases resistance*.—Has been observed to be highly resistant to powdery mildew caused by *Podosphaera macularis*) and leaf spot caused by *Pseudomonas cichorii*.

*Root description*.—Fibrous when young, becoming more fleshy with age.

*Propagation*.—Stem cuttings.

*Growth rate*.—Moderate.

Stem description:

*Shape*.—Rounded, solid.

*Stem color*.—Young 144A, mature 146A.

*Stem size*.—Main stem average 3 cm in length (excluding peduncles) and 4 mm in width, lateral branches up to 3 cm in length (excluding peduncles) and 2 mm in width.

*Stem surface*.—Young; slightly ridged and very slightly glossy, mature; slightly ridged and dull.

*Branching habit*.—An average of 7 main branches, each main branch has 3 to 4 lateral branches.

*Internode length*.—Variable, up to 2 cm.

Foliage description:

*Leaf division*.—Simple.

*Leaf margins*.—Entire to deeply tri-fid (almost leaflet-like), entire and lobes of tri-fid leaves very sparsely covered with short bristly hairs; 0.5 mm in length and NN155C in color.

*Leaf size*.—Simple; up to 7 cm in length and 6 mm in width, trifid; central lobe an average of 5 cm in length and 4 cm in width and lateral lobes an average of 3.5 cm in length and 2 cm in width.

*Leaf shape*.—Lanceolate.

*Leaf base*.—Attenuate.

*Leaf apex*.—Narrowly acute.

*Leaf venation*.—Pinnate, not prominent, coloration same as leaf on both surfaces.

*Leaf attachment*.—Sessile.

*Leaf arrangement*.—Opposite.

*Leaf surface*.—Young and mature upper and lower surfaces are glabrous.

*Leaf color*.—Young upper surface; 144A, mature upper surface; 146A, young lower surface; 144B, mature lower surface; 146B.

Flower description:

*Inflorescence type*.—Composite with ray florets surrounding disk florets in the center, forming a radiant head, inflorescences are borne on terminals arising from leaf axils.

*Lastingness of inflorescence*.—About 10 days until senescence of ray florets, bracts and disk florets are persistent.

*Fragrance*.—None.

*Quantity of inflorescences*.—An average of 5 per lateral branch, blooms are continuously produced until frost.

*Inflorescence size*.—Up to 1 cm in depth and up to 5.5 cm in diameter with disk portion up to 1.2 cm in width.

*Inflorescence buds*.—An average of 5 mm in depth and 7 mm in diameter, shape is spherical and flattened, color is 146B.

*Peduncle*.—Strong, average of 15 cm in length and 2 mm in diameter, 144A in color, surface is slightly ridged, dull and slightly satiny.

Involucral bracts:

*Bract number*.—Two rows of 8.

*Bract arrangement*.—20% fused and somewhat reflexed when flower is fully open and becoming horizontal after ray florets drop.

*Bract size*.—Inner bracts; an average of 8.5 mm in length and 2 mm in width, outer bracts; up to 6 mm in length and 3 mm in width.

*Bract color*.—Outer bracts; 146A on both surfaces, inner bracts; translucent, both surfaces 146A, outer edges N144A.

*Bract texture*.—All surfaces glabrous.
*Bract apex*.—Acute.
*Bract base*.—Truncate.
*Bract margins*.—Entire.
*Bract shape*.—Lanceolate.

Ray florets (pistillate):
*Number*.—8.
*Shape*.—Oblanceolate, appearance of three to four longitudinal sections with center section longer, overlapping.
*Size*.—An average of 2.2 cm in length and 1.3 cm in width.
*Apex*.—Varies between 3 to 4 lobes, acute to blunt overall.
*Base*.—Cuneate.
*Margins*.—Entire on sides, lobed at apex.
*Aspect*.—Held vertical.
*Texture*.—Both surfaces glabrous and satiny.
*Color*.—When opening upper surface; a blend of 46A and 187A, when opening lower surface; 4A, when fully open upper surface; a blend of 185A and 187A at the base fading to a blend of N45B and 185A towards the apex, blotched with NN155C occasionally at the apex, when fully open lower surface; a blend of 11A and 183A.

Disk florets (perfect):
*Number*.—An average of 100.
*Shape*.—Tubular, corolla is fused, flared at apex.
*Size*.—About 6 mm in length and 1 mm in width.
*Color*.—En masse; 14A, corolla; base (tube) is 12B in color and translucent, flared portion is 13A.
*Receptacle*.—About 8 mm in diameter and 4 mm in depth, 145C in color.

Reproductive organs:
*Presence*.—Disk florets are perfect, ray florets are pistillate.
*Gynoecium*.—1 Pistil, 5 mm in length, style is very fine and about 154CA in color and translucent, bifid pilose stigma is 14A in color with branches about 1 mm in length and recurved, ovary is 2 mm in length, 1 mm in width, inferior, and 11A in color.
*Androcoecium*.—5 stamens, fused into tube surrounding style, 1 mm in length and 0.5 mm in width, blend of 200A and N199C in color, no pollen was observed.
*Fruit/seed*.—No fruit or seed development was observed, plants have been observed to be nearly sterile.

It is claimed:

1. A new and distinct cultivar of *Coreopsis* plant named 'Red Elf' as herein illustrated and described.

* * * * *